United States Patent

Majewski et al.

[11] Patent Number: 5,864,141
[45] Date of Patent: Jan. 26, 1999

[54] COMPACT, HIGH-RESOLUTION, GAMMA RAY IMAGING FOR SCINTIMAMMOGRAPHY AND OTHER MEDICAL DIAGOSTIC APPLICATIONS

[75] Inventors: Stanislaw Majewski; Andrew G. Weisenberger, both of Grafton; Randolph F. Wojcik, Yorktown; Daniela Steinbach, Williamsburg, all of Va.

[73] Assignee: Southeastern Univ. Research Assn., Newport News, Va.

[21] Appl. No.: 898,731

[22] Filed: Jul. 23, 1997

[51] Int. Cl.$^6$ .................................................. G01T 1/20
[52] U.S. Cl. ................... 250/363.02; 250/363.1; 250/367
[58] Field of Search ............... 250/363.02, 363.1, 250/367, 368, 369, 207, 214 VT

[56] References Cited

U.S. PATENT DOCUMENTS

| | | | |
|---|---|---|---|
| 4,066,908 | 1/1978 | Farukhi et al. | 250/483.1 |
| 4,109,155 | 8/1978 | Tschunt et al. | 250/363.1 |
| 4,700,075 | 10/1987 | Kurz et al. | 250/368 |
| 4,792,686 | 12/1988 | Karcher et al. | 250/363.1 |
| 4,929,835 | 5/1990 | Yamashita et al. | 250/369 |
| 5,148,029 | 9/1992 | Persyk et al. | 250/363.02 |
| 5,220,170 | 6/1993 | Cox et al. | 250/370.09 |
| 5,401,969 | 3/1995 | Basler | 250/363.1 |
| 5,521,378 | 5/1996 | Roscoe et al. | 250/269.6 |
| 5,594,253 | 1/1997 | Bueno et al. | 250/368 |

Primary Examiner—Constantine Hannaher
Assistant Examiner—Darren M. Jiron

[57] ABSTRACT

A high resolution gamma ray imaging device includes an aluminum housing, a lead screen collimator at an opened end of the housing, a crystal scintillator array mounted behind the lead screen collimator, a foam layer between the lead screen collimator and the crystal scintillator array, a photomultiplier window coupled to the crystal with optical coupling grease, a photomultiplier having a dynode chain body and a base voltage divider with anodes, anode wire amplifiers each connected to four anodes and a multi pin connector having pin connections to each anode wire amplifier. In one embodiment the crystal scintillator array includes a yttrium aluminum perovskite (YAP) crystal array. In an alternate embodiment, the crystal scintillator array includes a gadolinium oxyorthosilicate (GSO) crystal array.

6 Claims, 1 Drawing Sheet

COMPACT, HIGH-RESOLUTION, GAMMA RAY IMAGING FOR SCINTIMAMMOGRAPHY AND OTHER MEDICAL DIAGOSTIC APPLICATIONS

BACKGROUND OF THE INVENTION

1. Field of the Invention

The present invention pertains to gamma ray imaging devices and more particularly to high-resolution, gamma ray imaging device for scintimammography and other medical diagnostic applications.

2. Related Prior Art

Gamma ray imaging devices have reached a point in their development that a general multi-purpose imaging device is not feasible. Presently, problems relate to the generation of gamma rays and their detection.

Application specific detectors useful for scintimammography must have a suitable physical geometry for breast imaging, be able to efficiently detect and locate gamma rays emitted from lesions in breast tissue, and at the same time efficiently reject scattered radiation from the patient body. These gamma ray imagers could be used as additional diagnostic tools used in conjunction with X-ray mammography. The following articles generally are representative of the state of the art regarding scintimammography and apparatus used in breast imaging.

An article titled "Scintillating Array Gamma Camera for Clinical Use", written by R. Pani et al. relates to dedicated gamma cameras for specific clinical application. These cameras are based on the use of position sensitive photo multiplier tubes (PSPMT). The main intrinsic limitation of large area position sensitive photomultiplier tube (5" diameter) is the photocathode glass window. Coupling planar scintillation crystal strongly affects the useful active area and the intrinsic spatial resolution. To overcome this limitation the first 5" diameter gamma camera was developed that consisted of Hamamatsu R3292 position sensitive photomultiplier tube coupled to 50×50 YAP: Ce scintillating array. The array pixel size was 2×2 mm$^2$ and the overall dimension of multi-crystal was 10×10×1 cm$^3$. Resistive chains to calculate the centroid were used. A scintillating array produces a focused light spot minimizing the spread introduced by position sensitive photomultiplier tube glass window. The intrinsic spatial resolution resulted between 2 mm and 2.7 mm. The position linearity and useful active area resulted in good agreement with the intrinsic one obtained by light spot irradiation. The real limitation resulted the poor energy resolution of crystals (forty percent) and the poor uniformity response of position sensitive photomultiplier tube (within +or −fifteen percent). A correction matrix was then carried out by which fifty-seven percent of total energy resolution was obtained. The camera operates as Single Photon Emission Mammography (SPEM) and is producing breast functional images for malignant tumor detection under breast compression and in the same geometry of standard x-ray mammography.

An article titled "Multi-crystal YAP: Ce Detector System for Position Sensitive Measurements", written by R. Pani et al in Nuclear Instruments and Methods in Physics Research, A 348 (1994) relates to Yttrium aluminum perovskite (YAP:Ce) scintillation crystal. YAP:Ce has a light efficiency of about forty percent relative to NaI. Because of the yttrium atomic number (Z=39) and the relatively high density (5.37 g/cm$^3$) this crystal has a good gamma-ray absorption. Furthermore it is not hygroscopic and is inert. Its peculiarity consists of material processing that provides us with crystal pillars down to 0.3×0.3 mm$^2$ aperture size and up to some centimeters in length. An array consisting of 11×22 YAP:Ce elements was made where each crystal has an aperture of 0.6×0.6 mm$^2$ and a length of 7 mm. Each scintillation crystal is optically separated by a reflective material resulting in a separation layer between elements of about 5 $\mu$m. The multicrystal detector is optically coupled to a Hamamatsu Position Sensitive Photomultiplier Tube (R2486). The intrinsic spatial resolution of the position sensitive photomultiplier tube is better than 0.3 mm but it is strongly dependent on the Point Spread Function (PSF) generated on the photocathode. The multicrystal detector very well matched the position sensitive photomultiplier tube characteristics resulting in a spatial resolution of about 0.7 mm at 140 keV ($^{99m}$Tc) gamma irradiation.

An article titled "Toward a Nuclear Medicine with Submillimeter Spatial Resolution", written by L. H. Barone et al in *Nuclear Instruments and Methods in Physics Research, A* 360 (1995) relates to the HIRESPET Collaboration developing a new concept of a gamma camera with sub-millimeter spatial resolution. The first prototype consists of a small field size gamma camera based on a position sensitive photomultiplier tube (PSPMT) coupled to a scintillation crystal. The intrinsic spatial resolution of the position sensitive photomultiplier tube is better than 0.3 mm. The scintillation crystal consists of yttrium aluminum perovskite (YAP: Ce). It has a light efficiency of about forty percent relative to NaI, a good gamma radiation absorption (z=39) and a high density (5.37 g/cm$^3$). It is inert and not hygroscopic. To match PSPMY characteristics, a special crystal assembly has been made consisting of a bundle of yttrium aluminum perovskite pillars, where a single crystal has the transversal dimension of 0.6×0.6 mm$^2$ and a thickness ranging between 1 mm and 28 mm. Each scintillation pillar is optically separated from the other by a reflective layer of 5 $\mu$m thick. The preliminary results obtained from the gamma camera prototype (yttrium aluminum perovskite camera) show spatial resolution values ranging between 0.6 and 1 mm and an intrinsic detection efficiency comparable with a standard Anger camera.

An article titled "Pixellated CsI(TI) arrays with position-sensitive PMT readout", written by A. Truman et al in *Nuclear Instruments and Methods in Physical Research, A* 353 (1994), relates to the position and energy resolution characteristics of three scintillation detectors viewed by a three square inch position sensitive photomultiplier tube that have been measured as a function of photon energy. Pixellated detectors having a pitch that ranges between 1.5 mm and 3.5 mm have been studied. The FWHM of the distribution in measured positions was as little as 0.9 mm at 122 keV. In this case, the tube was read out using individual amplifiers to record the charge detected on each individual anode wire and the location found using a peak fitting algorithm. Comparative measurements were also made using the conventional hardware centroiding technique.

SUMMARY OF THE INVENTION

As stated previously, application specific detectors useful for scintimammography must have a suitable physical geometry for breast imaging. In addition, they must be able to efficiently detect and locate gamma rays emitted from lesions in breast tissue, and at the same time efficiently reject scattered radiation from the patient body. These application specific gamma ray imagers could be used as additional diagnostic tools used in conjunction with X-ray mammography.

The apparatus of the present invention is a camera that consists of a parallel-hole collimator placed in front of a yttrium aluminum perovskite (YAP) crystal array optically coupled with optical grease to a 5" round position sensitive photomultiplier tube.

The yttrium aluminum perovskite crystal array consists of one thousand twenty-four 3×3×10 mm³ crystals that are optically separated by 5 micron thin deposited aluminum layers and glued together in units of 512 crystals (16×16) forming an approximately five centimeter square detector modules. Four units are mounted in a 2×2 array on the position sensitive photomultiplier tube. The crystals at the very corner of the 10 cm² crystal array are imaging. Fifty-six anode wires arranged in sectors of four wires each are directly connected to fourteen amplifiers located in the detector head. The setup is encased by ⅛" thick lead shield to avoid unwanted counts of background radiation. The collimator is 35 mm long with hexagonal holes of size d=1.22 mm. Its lamina are 0.15 mm thick.

Anode wire groups of four wires each are used to reduce the number of channels to the instrument by a factor of four. All anode sector signals are amplified in low noise amplifiers and delayed before entering fourteen individual ADC channels.

Determination of the position of gamma interaction in the yttrium aluminum perovskite matrix was achieved by a calculation of the center of gravity (COG) of the signal distribution on the x and y anode sectors of the position sensitive photomultiplier tube and identifying the interacting yttrium aluminum perovskite crystal.

Based on the ability to separate individual crystal pixels and the resulting possibility to set their individual energy cuts, scatter rejection can be performed efficiently in the imager of the present invention.

DESCRIPTION OF THE PREFERRED EMBODIMENT

Early detection of breast cancer can lead to a high probability of cure. Currently, virtually all mammography is performed using X-ray radiography with screen film systems and dedicated mammographic X-ray units. However, because breast tumors are similar in X-ray attenuation to fibroglandular tissue, small tumors are difficult to detect, particularly in women with radiodense breasts. Furthermore, the inability of X-ray mammography to provide information on tumor functional or metabolic activity often necessitates surgical or core needle biopsy to determine whether the mass is benign or malignant. About seventy percent of biopsies are performed on benign lesions. Diagnostic methods of nuclear medicine based on gamma emissions such as scintimammography (with radioactive isotopes of $^{201}$Tl or $^{99m}$Tc) and positron emission mammography (PEM) (with $^{18}$F-labeled glucose of estrogenic steroids) have been shown to exhibit high sensitivity and specificity for cancers in patients with positive X-ray mammograms.

Figure 1:
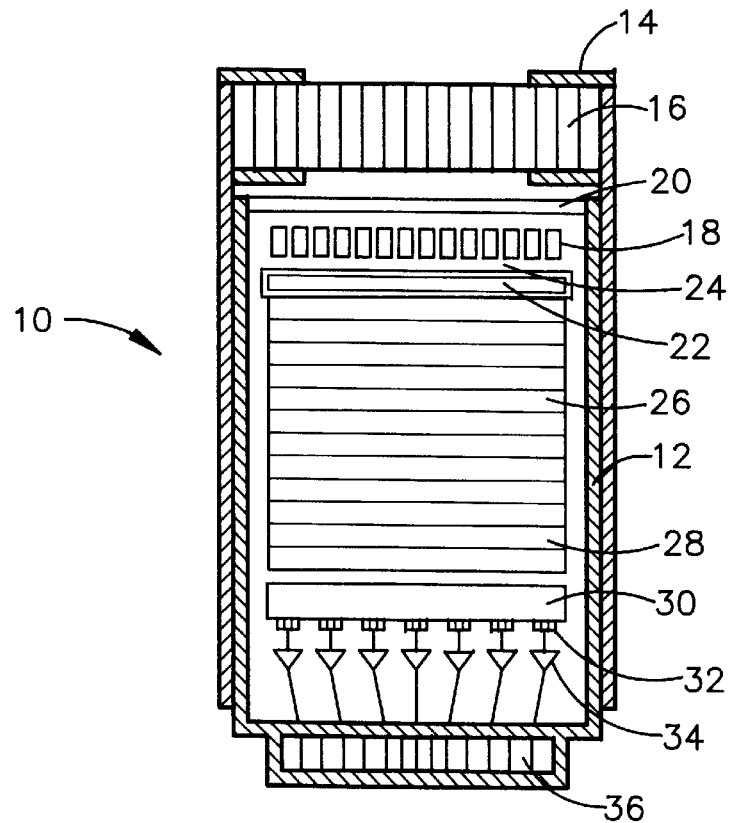
FIG. 1 is a schematic diagram of a gamma camera utilizing a yttrium aluminum perovskite array.

Referring to FIG. 1, a diagram of a gamma camera 10 is illustrated as contained in an aluminum housing 12 having a lead screen 14 holding a collimator 16 in place. Collimator 16 is placed in front of and is coupled to yttrium aluminum perovskite (YAP). crystal array 18 with a layer of foam 20. Yttrium aluminum perovskite array 18 is placed on PMT window 22 using optical coupling grease 24. Photomultiplier tube window 22 covers dynode chain 26 of position sensitive photomultiplier tube 28 which is mounted on photomultiplier tube base 30 and voltage divider 32. Anode wire amplifiers 34 receive signals from voltage divider 32 and provides an input to multiple signal connecter 36.

Other suitable crystal arrays such as cesium iodide, sodium iodide or gadolinium oxyorthosilicate (GSO) may also be used.

The camera or apparatus of the present invention consists of a parallel hole lead collimator 16 (by Precise Co.) placed in front of yttrium aluminum perovskite crystal array 18 (from Preciosa via Scionix) optically coupled with Bicron 6630-00001 optical grease 24 to a five inch round R3292 Hamamatsu position sensitive photomultiplier tube 28. While lead is the preferred choice, other heavy metals such as tantalum and tumgster may also be used.

Yttrium aluminum perovskite crystal array 18 consists of one thousand twenty-four 3×3×10 mm³ crystals that are optically separated by 5 micron thin deposited aluminum layers and glued together in units of 512 crystals (16×16) forming an approximately five centimeter square thin walled detector modules in an aluminum tray that is painted with white paint on the outside. Its lamina are 0.15 mm thick. Four units are mounted in a 2×2 array on position sensitive photomultiplier tube 28. The crystals at the very corner of the 10 cm² crystal array 18 are protruding over the physical limits of the face of position sensitive photomultiplier tube 28 and are therefore not used for imaging. Fifty-six anode wires arranged in sectors of four wires each are directly connected to fourteen amplifiers 34 located in the detector head. The set-up is encased by ⅛ " thick lead shield to avoid unwanted counts of background radiation. Collimator 16 is 35 mm long with hexagonal holes of size d=1.22 mm. Four units are mounted on the position sensitive photomultiplier tube 28.

To reduce the number of individual analog channels while still retaining the advantage of local electronic readout anode wire groups of four wires each are used to reduce the number of channels to the instrument by a factor of four. This is done as opposed to integral methods such as current division or delay lines. There is no decrease in position resolution by this operation, because the deceased granularity of readout was compensated by a resulting improvement in the signal-to-noise ratio. The 28x+28y anode wire problem was reduced to 7x+7y wire groups. All anode sector signals were amplified in low noise LeCroy TRA 1000 amplifiers and delayed by 50 nsec before entering fourteen individual ADC channels.

The electronic signal from the last dynode of the position sensitive photomultiplier tube 28 is used after inverting and then passing through discriminator electronics to detect an event and determine if the signal amplitude is above a desired background and noise threshold, and to generate a 150 nsec wide gate to FERA ADCs. The data acquisition system was based on FERA ADCs from LeCroy and a Power Macintosh 8100 work station as the host computer (not shown) running the Kmax data acquisition software from Sparrow Corporation.

Determination of the position of gamma interaction in yttrium aluminum perovskite array 18 matrix was achieved by a calculation of the center of gravity (COG) of the signal distribution on the x and y anode sectors of position sensitive photomultiplier tube 28 and identifying the interacting yttrium aluminum perovskite crystal in crystal array 18.

Raw images obtained from the camera show distorted crystal positions because of non-uniformities in the response of position sensitive photomultiplier tube 28. Since the relative position of each crystal is known and the crystals can be defined in the raw image, a distortion correction is easily achieved by channeling the data identified to belong to a particular crystal into the crystal's appropriate box in the corrected image. The box regions of the corrected image have been obtained using a flood image and after the borders of each region of crystal array 18 were defined.

The individual energy responses from previously identified yttrium aluminum perovskite crystals-pixels have been used to set energy cut requirements on the data used to produce the image. Energy cuts were set individually below the 141 keV photopeak so that only the majority of events coming from the photon interaction would be allowed to contribute to the image and not to the background scatter.

This method of scatter rejection allowed for an efficient correction of gain variations across the face of position sensitive photomultiplier tube 28 as well as of variations between responses from individual crystals-pixels of crystal array 18. It treated each 3×3 mm$^2$ region as a pixel with its own unique energy cut.

It was demonstrated that an optimized readout of a 5" Hamamatsu R3292 PMT with seven four wire anode groups on both x and y coordinates, low-noise amplifiers and a COG algorithm utilizing truncated signal distributions on anode wire sections with a simple charge fraction (F-factor) criterion can lead to a practical small FOV gamma imager when coupled to an array of 3 mm crystals-pixels of a bright scintillator such as yttrium aluminum perovskite. Based on the ability to separate individual crystal pixels and the resulting possibility to set their individual energy cuts, scatter rejection can be performed efficiently in the imager of the present invention.

The choice of 3*3 mm$^3$ transversal crystal-pixel size makes it possible to resolve the different crystals and is therefore crucial for the subsequent data processing which treats the output from each crystal region individually to correct for crystal-to-crystal scintillation output variations as well as local position sensitive photomultiplier tube gain variations. The individual crystals-pixels show variations in light output depending on their origin from the crystal boule and variations in surface treatment.

A crystal array with smaller pixels, for example 2*2 mm$^2$, would have made it much more difficult for individual array pixels to be distinguished and a different correction scheme would have to be used.

The center of gravity of the signals from seven x wire groups was obtained from a well known calculation. A corresponding procedure was used for the calculation of the COG in the y direction. The resulting coordinates marked an event in the raw image plane.

The relative signal amplitudes on the seven wire sections, that is, the relative charge distribution on the anode wire groups, occurs in two events. Most of the charge is collected on two to three output channels with the other channel outputs practically at zero level. Small fluctuations in the charges collected on these additional channels occur due to statistics and tube/electronics noise and can distort the COG calculation in equation. To keep these fluctuations from influencing the COG calculations, only channels carrying charge above some value (f-factor) of the total charge were allowed to contribute.

The effect of the charge fraction (f-factor) on obtained crystal separation was studied. If no f-factor is used to obtain an image, crystal regions in the central region are not well separated. If too large an f-factor is used, artifacts are introduced because the number of wire groups contributing to the COG calculation might be reduced to one or two in many cases and the image contains a disproportional number of events centered on a wire group. An f-factor of 0.05 is preferred. A Gaussian Peak Finding fit was tested with the Levenberg-Marquardt method. Only small improvement was obtained as compared to the COG method with an f-factor.

Raw images obtained from the camera show distorted crystal positions due to non-uniformities in the position sensitive photomultiplier tube response. Since the relative position of each crystal is known and the crystals can be defined in the raw image, a distortion correction is easily achieved by channeling the data identified to belong to a particular crystal into that crystal's appropriate rectangle in the corrected image.

The individual energy spectra from yttrium aluminum perovskite crystals-pixels have been used to set energy cut requirements on the data used to produce the image. Energy cuts were set individually at the channel indicated in each case by the dashed line at the left side of the 141keV photopeak so that only events with counts above that channel would be allowed to contribute to the image.

This method of scatter rejection allowed for an efficient correction of gain variations across the face of the position sensitive photomultiplier tube as well as of variations between responses from individual crystals-pixels. It treated each 3*3 mm$^2$ region as a pixel with its own unique energy cut.

Higher energy cuts coincided with regions of higher gain of the position sensitive photomultiplier tube as specified by the manufacturer. As mentioned above, the corner regions of the crystal array were not used for image formation as they were not in the field of view of the position sensitive photomultiplier tube. The energy cuts for the corner regions have therefore been set to a large value (2050) beyond the dynamic range of the ADC (11 bits).

During data acquisition, events were recorded both in a raw image histogram with a minimal global energy cut requirement and a corrected image histogram. The corrected image events were distributed in the appropriate crystal regions only if they were higher in energy than the cut set for that region. Each crystal region was assigned four pixels and the events were randomly distributed within the appropriate four pixels. The corrected image was then multiplied by 1000 and divided by a high statistics flood taken under the same conditions as the image. Finally, the data was filtered and smoothed using NIH Image software.

After a series of tests with point sources and standard thyroid phantoms, studies with breast phantoms containing lesions with realistic size and concentrations were performed. Two phantoms were constructed, one simulating a breast under compression and one shaped like a non-compressed breast. Each phantom contained three small balloons with maximum capacities of 1, 1.5, and 2 cc. A concentration in the breast tissue of approximately 40 nanoCi per cc of blood was assumed at imaging time. This corresponds to a one percent accumulation following an injection of 20 mCi into a patient blood volume of 5 liters. Thus, the 500 cc containers that simulated the breast were filled with about 20 microCi of $^{99m}$Tc. The concentration of radionuclide in the tumor was assumed to be five to ten times that of the breast tissue. Imaging times, breast compression, lesion size, and effect of scatter from radiation emanating from heart and liver were studied in the investigation.

Figure 2:
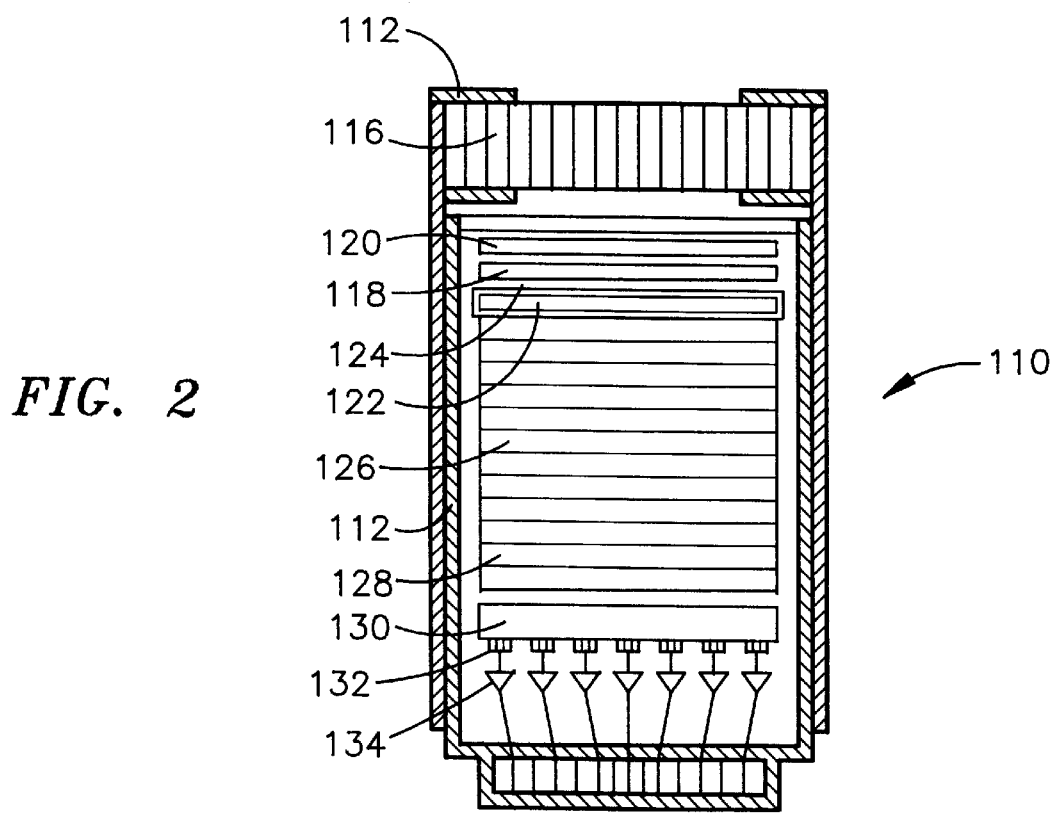
FIG. 2 is a schematic diagram of a gamma camera using a gadolinium oxyorthosilicate array.

Referring now to FIG. 2, a diagram of an alternate embodiment of a gamma camera 110 of the present invention is illustrated as contained in an aluminum housing 112 having a lead screen 114 holding a collimator 116 in place. Collimator 116 covers a gadolinium oxyorthosilicate (GSO) array 118 and is coupled thereto with a layer of foam 120. Gadolinium oxyorthosilicate array 118 is placed on PMT window 122 using optical coupling grease 124. Photomultiplier tube window 122 covers dynode chain 126 of position sensitive photomultiplier tube 128 which is mounted on photomultiplier tube base 130 and voltage divider 132. Anode wire amplifiers 134 receive signals from voltage divider 132 and provide an input to multiple signal connecter 136. In general, gadolinium oxyorthosilicate (GSO) array 118 of FIG. 2 may be substituted for yttrium aluminum perovskite (YAP) crystal array 18 of FIG. 1.

The present invention provides a gamma imaging detector based on a 10 cm by 10 cm yttrium aluminum perovskite (YAP) crystal array made of 3×3×10 mm$^3$ crystals-pixels and a 5" diameter Hamamatsu R 3292 position sensitive photomultiplier tube (PSPMT). In an alternate embodiment, a gadolinium oxyorthosilicate (GSO) crystal array is used. After the readout of the position sensitive photomultiplier tube was optimized a resolution of about 3mm @ 140 keV was obtained using only fourteen (7x, 7y) anode wire sections in lieu of the standard 28×28 individual crossed-wires. Because individual crystals are well-separated and identified, a simple but effective position distortion correction is possible based on a flood measurement. Efficient scatter rejection is provided by placing individual energy windows on scintillation signals coming from each crystal-pixel. Measurements were made with thyroid phantoms and compressed as well as non-compressed breast phantoms with simulated lesions. The phantoms contained appropriate concentrations of $^{99m}$Tc emitting 140keV gamma radiation. The detector combined good performance with small size and economical makeup. After final phantom tests we are planning to use it in clinical trials as a small field-of-view scintimammography camera.

While there has been illustrated and described a particular embodiment of the present invention, it will be appreciated that numerous changes and modifications will occur to those skilled in the art, and it is intended in the appended claims to cover all those changes and modifications which fall within the true spirit and scope of the present invention.

We claim:

1. A high resolution gamma ray imaging device comprising:

an aluminum housing;

a heavy metal screen collimator, at an opened end of said housing;

a crystal scintillator array mounted behind said screen collimator;

foam layer between said screen collimator and said crystal scintillator array;

photomultiplier window coupled to said crystal with optical coupling grease;

photomultiplier having a dynode chain body and a base voltage divider, with anodes;

anode wire amplifiers, each connected to four anodes; and multi pin connector having pin connections to each anode wire amplifier.

2. The high resolution gamma ray imaging device according to claim 1 wherein said crystal scintillator array includes a yttrium aluminum perovskite (YAP) crystal array.

3. The high resolution gamma ray imaging device according to claim 2 wherein said yttrium aluminum perovskite (YAP) crystal array includes a 10 cm by 10 cm yttrium aluminum perovskite (YAP) crystal array made of 3×3×1 mm$^3$ crystals pixels.

4. The high resolution gamma ray imaging device according to claim 1 wherein said crystal scintillator array includes a gadolinium oxyorthosilicate (GSO) crystal array.

5. The high resolution gamma ray imaging device according to claim 4 wherein said gadolinium oxyorthosilicate (GSO) crystal array includes a 10 cm by 10 cm gadolinium oxyorthosilicate crystal array made of 3×3×10 mm$^3$ crystal-spixels.

6. The high resolution gamma ray imaging device according to claim 1 wherein said heavy metal is lead.

* * * * *